United States Patent [19]

Pawloski

[11] Patent Number: 4,774,348

[45] Date of Patent: Sep. 27, 1988

[54] PREPARATION OF HALOGENATED PHOSPHORATES EMPLOYING TRIOLS

[75] Inventor: Chester E. Pawloski, Bay City, Mich.

[73] Assignee: The Dow Chemical Company, Midland, Mich.

[21] Appl. No.: 849,596

[22] Filed: Apr. 8, 1986

[51] Int. Cl.$^4$ ................................................. C07S 9/09
[52] U.S. Cl. .................................................... 558/91
[58] Field of Search ................................... 558/91, 84

[56] References Cited

U.S. PATENT DOCUMENTS

| | | | |
|---|---|---|---|
| 1,936,985 | 5/1933 | Lommel et al. ...................... | 358/91 |
| 3,132,169 | 8/1964 | Birum et al. ......................... | 558/91 |
| 3,324,205 | 2/1967 | Carpenter et al. .................. | 558/91 |
| 4,046,719 | 4/1977 | Stanabach et al. .................. | 558/203 |
| 4,083,825 | 6/1978 | Albright et al. ..................... | 558/203 |
| 4,240,953 | 2/1980 | Albright .............................. | 558/203 |

OTHER PUBLICATIONS

*Chemical Week*, 137(18), 17 (Oct. 30, 1985).
Rose; Honkomp & Hach, "A New High Efficiency Flame Retardant for Flexible Polyurethane Foam" (Oct. 23–25, 1985).
Great Lakes Chemical Corp., Product Information on Fire Master ®836 ® (Oct. 18, 1985).

*Primary Examiner*—Anton H. Sutto
*Attorney, Agent, or Firm*—Christopher J. Rudy

[57] ABSTRACT

Included is a process to prepare a halogenated phosphorate-containing product comprising serially contacting (a) a triol with a phosphorus trihalide, (b) a halogenating agent and (c) an oxirane, under conditions sufficient to prepare the halogenated phosphorate-containing product. For example, 2-methyl-2-(hydroxymethyl)-1,3-propanediol, phosphorus trichloride, bromine and ethylene oxide can be employed to prepare a mixture of (2,2-bis(bromomethyl)propyl)(2-bromoethyl)(2-chloroethyl) phosphorate and (2-bromoethyl)bis(2-chloroethyl)phosphorate.

8 Claims, No Drawings

PREPARATION OF HALOGENATED PHOSPHORATES EMPLOYING TRIOLS

FIELD

This invention concerns a process to prepare phosphorus-containing organic compounds. It can also concern these compounds and their use, especially as a flame retardant in flexible polyurethane foams.

BACKGROUND

Lommel et al., U.S. Pat. No. 1,936,985 (1933) (incorporated herein by reference), disclose the production of certain phosphorus and phosphoric acid esters which may contain halogen. It is taught that the compounds reduce the flammability of organic materials if incorporated therein.

Birum et al., U.S. Pat. No. 3,132,169 (1964) (incorporated herein by reference), disclose the preparation of certain phosphate esters which contain both chlorine and bromine. It is taught that polyurethanes, for example, insulating foams and resin bases for curable coatings and adhesives, may be made flame-retardant by the addition of the phosphate esters in amounts from 2 percent to 25 percent by weight of the polyurethane. It is also taught that simultaneous plasticizing results and the use of the phosphate esters in the polyurethane foams taught therein (i.e., rigid foams) can increase flexibility and in some applications improve the mechanical properties of the foams.

Stanabach et al., U.S. Pat. No. 4,046,719 (1977) (incorporated herein by reference), disclose that certain trihaloneopentyl-containing haloalkyl phosphate esters are flame retardants for normally flammable resinous compositions. It is taught that tribromoneopentylbis(-mono- or dichloro $C_{2-4}$ alkyl)phosphates, tribromoneopentyl(mono- or dichloro $C_{2-4}$ alkyl)phenyl phosphates and bis(tribromoneopentyl) (mono- or dichloro $C_{2-4}$ alkyl)phosphates impart non-scorch and non-drip characteristics to foams.

Albright, U.S. Pat. No. 4,240,953 (1980) (incorporated herein by reference), disclose certain hydrogen-, chloro- and bromo-substituted neopentylbis(dihaloalkyl)phosphates (halo:chloro; bromo). It is disclosed that certain bis(dichloroalkyl)phosphates possess light-stability properties and that when the substituted neopentyl group is 2,2-dimethyl-3-halopropyl, the phosphates are of relatively low viscosity.

Albright et al., U.S. Pat. No. 4,083,825 (1978) (incorporated herein by reference), disclose that certain hydrogen-, chloro- and bromo-substituted neopentylbis(-chloro-containing $C_{2-3}$ alkyl)phosphates substantially solve the problem of scorch in flame-retardant polyurethanes.

What is lacking and which is needed is another process to prepare halogenated phosphorates which can be used to prepare such phosphorates. The process shoudl be efficient and selective.

SUMMARY

The invention is a process to prepare a halogenated phosphorate-containing product comprising serially contacting (A) a triol with a phosphorus trihalide;
(B) a halogenating agent; and
(C) an oxirane, under conditions sufficient to prepare the halogenated phosphorate-containing product.

The process is highly efficient and selective. The halogenated phosphorate-containing product is useful in the preparation of flame-retardant polyurethane foams, especially flexible slabstock foams preferably with little or no scorch or odor.

ILLUSTRATIVE EMBODIMENTS

The following preferred general sequence further illustrates the process:

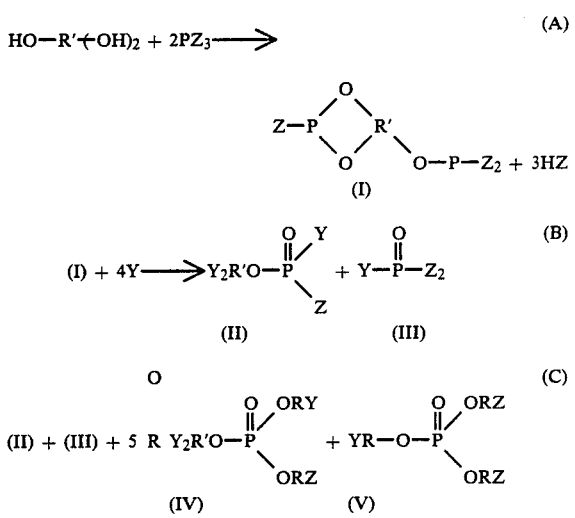

wherein

R and R' are residues of the oxirane and triol, respectively;

Y is separately at each occurrence F, Cl, Br or I, preferably F, Cl or Br, more preferably Cl or Br; and Z is separately at each occurrence F, Cl or Br, preferably Cl or Br.

The halogenated phosphorate product prepared may be substantially one halogenated phosphorate or may be a mixture of halogenated phosphorates. Preferably, the product is a mixture of halogenated phosphorates.

The halogenated phosphorate product prepared preferably contains a β-neocarbylbis(haloalkyl)phosphorate flame-retardant compound. The β-neocarbylbis(-haloalkyl)phosphorate flame-retardant compound is a haloalkyl phosphorus acid ester compound containing the β-neocarbyl and haloalkyl moieties. The β-neocarbyl moiety is a saturated carbon-containing moiety which has a quaternary (i.e., 4°) carbon bonded directly to a carbon which forms a bond connectable to the remaining part of the molecule. The β-neocarbyl moiety of the β-neocarbylbis(haloalkyl)phosphorate is thus connectable to the phosphorus through an oxygen such as in a phosphate ester. The β-neocarbyl moiety is alkyl or haloalkyl. The β-neocarbyl moiety of the β-neocarbylbis(haloalkyl)phosphorate is more preferably haloalkyl. The haloalkyl moiety is a saturated halo-substituted hydrocarbyl moiety with a 4° carbon. The haloalkyl moiety is likewise connectable to the phosphorus.

The β-neocarbylbis(haloalkyl)phosphorate-containing product prepared may also be substantially one phosphorate or may be a mixture of phosphorates. The β-neocarbylbis(haloalkyl)phosphorate flame-retardant compound is preferably a phosphate ester of the general formula

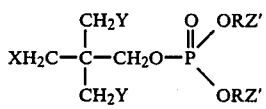

(VI)

wherein
X is H, Cl, Br or $C_{1-5}$ alkyl;
Y is separately at each occurrence Cl or Br, most preferably Br;
Z' is separately at each occurrence Cl or Br, most preferably one Z is Cl and the other Z is Br; and
R is separately at each occurrence an oxirane residue, more preferably a saturated hydrocarbyl of the formula $C_nH_{2n}$ wherein n is an integer selected from 2 to about 5, most preferably 2 or 3.

The other phosphorates present preferably correspond to the general formula

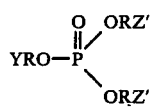

(VII)

wherein
R and Y are each as defined for the compound (VI) herein; and
Z' is separately at each occurrence Cl or Br, most preferably Cl. Preferably, the β-neocarbylbis(-haloalkyl)phosphorate-containing mixture is a phosphorate mixture of compounds such as the compounds (VI) and (VII). The mixture of compounds such as the compounds (VI) and (VII) is preferably in a molar ratio of about 1:1.

The first step (A) involves contacting the triol with the phosphorus trihalide. Preferably, conditions are those sufficient to prepare an acyclic and heterocyclic phosphite acid halide such as illustrated by compound I.

The triol employed is an organic compound containing three hydroxy moieties. Preferably, the triol is otherwise inert in relation to the phosphorus trihalide. Thus, the triol can contain moieties such as, for example, halo; cyano; ether; thioether; sulfoxy; and acyl ester.

Preferably, two of the three hydroxy moieties of the triol are positioned in a manner which can allow formation of a 5- to 7-membered heterocyclic phosphorus-containing ring with intermediate species. Of these heterocyclic rings, 5- and 6-membered rings are preferred.

The triol itself can be acyclic or cyclic. Preferably, the two hydroxy moieties which can allow the intermediate species ring formation are bonded to an acyclic part of the triol. More preferably, each hydroxy moiety of the triol is bonded to an acyclic part of the triol. Most preferably, the triol is acyclic.

The triol can be saturated or unsaturated. Most preferably, the triol is saturated. Triols can be such as those employed in copending U.S. patent application, filed Apr. 8, 1986 Ser. No. 849,590 filed 4-8-86 including triols such as those disclosed in copending U.S. patent application Ser. No. 799,777, filed Nov. 20, 1985 (both incorporated herein by reference). Exemplary triols include 1,2,3-propanetriol; 1,2,4-butanetriol; 1,2,10-decanetriol and 2,2-bis(hydroxymethyl)-1-octanol.

The triol employed is preferably a β-neocarbyltriol. The β-neocarbyltriol contains β-neocarbyl moiety hydroxylated with three hydroxy moieties. The β-neocarbyltriol is preferably a triol of the general formula $XH_2C-C+CH_2OH)_3$ wherein X is as defined herein. Exemplary β-neocarbyltriols include 2,2-bis(hydroxymethyl)-1-octanol and 2,2-bis(hydroxymethyl)-1-propanol.

The phosphorus trihalide employed can contain halides of bromide, chloride and fluoride, preferably bromide and chloride. The phosphorus trihalide is more preferably a compound such as phosphorus trichloride or phosphorus tribromide. phosphorus trichloride is most preferred.

Preferably, about one molar equivalent of the triol is added in portions to about 2 molar equivalents of the phosphorus trihalide at room temperature (i.e., about 20° C.) or below (e.g., ice water bath). Higher temperatures typically produce undesired by-products. If the phosphorus trihalide is added to the triol, even at cold temperatures, considerable amounts of by-products are typically produced.

The second step (B) involves subsqunt contact with the halogenating agent. Preferably, conditions are those sufficient to prepare phosphate acid halides such as illustrated by compounds II and III.

The halogenating agent of step (B) is a suitable source of halogen (other than from the phosphorus trihalides) which is imparted to the reaction mixture to prepare the β-neocarbylbis(haloalkyl)phosphorate-containing product. The halogenating agent can be a halogen-containing compound such as elemental iodine, elemental bromine, elemental chlorine and elemental fluorine and mixed halogen compounds, for example, bromine chloride. Elemental bromine is most preferred.

The halogenation is exothermic, and it is preferably carried out at room temperature or below. Higher temperatures typically produce a by-product of halogenated alkanes. Preferably, about 4 molar equivalents of halogenating agent in step (B) are employed, based on the equivalents of halo moieties available for reaction. Thus, for example, about 2 molar equivalents of elemental bromine are preferably employed in step (B).

The third step (C) involves subsequent contact with the oxirane. Thus, the halogenated phosphorate-containing product can be prepared.

The oxiranes employed can include various types of oxiranes such as an alkyl epoxide such as ethylene oxide, propylene oxide, butylene oxides, 1,2-epoxydodecane and 1,2-epoxyhexadecane; an unsaturated aliphatic epoxide such as 3,4-epoxy-1-butene, 1,2-epoxy-5-hexene and 1,2-epoxy-7-octene; an aryl-containing epoxide such as 1,4-epoxy-1,4-dihydronaphthalene; an unsaturated ether epoxide such as allyl glycidyl ether; a dealkylatable epoxie such as t-butyl glycidyl ether; and a halogenated epoxide such as epichlorohydrin, epibromohydrin and 2,4,6-tribromophenol glycidyl ether.

The halogenated phosphorate product containing a residue of an unsaturated epoxide is preferably halogenated with the halogenating agents of step (B). The halogenating agents of step (B), especially bromine, are preferred.

The halogenated phosphorate product containing a residue of a dealkylatable epoxide is preferably dealkylated to obtain a hydroxylated-halogenated phosphorate product of low viscosity. The dealkylation is preferably carried out with an acid such as phosphoric acid or an aryl sulfonic acid such as disclosed by Ginter et al., U.S. Pat. No. 4,298,709 (1981) (incorporated herein by reference).

The preparation may be carried out neat or in the presence of a diluent. Preferably, an inert, liquid diluent is employed. Preferred inert, liquid diluents include the halogenated alkanes such as carbon tetrachloride, methylene chloride, chloroform and 1,2-dichloroethane. The preferred halogenated alkane is methylene chloride.

The preparation is preferably carried out under an inert atmosphere such as argon and nitrogen. Nitrogen is preferred.

The oxirane addition is typically exothermic, most notably so in the presence of catalytic amounts of a catalyst such as Lewis acid catalysts, for example, titanium, tetrachloride and aluminum tirchloride. The oxirane reaction is preferably carried out at from room to elevated temperatures. Preferred elevated temperatures include temperatures of about 85° C., more preferably about 65° C. and most preferably about 45° C. Preferably, at least about 5 molar equivalents of the oxirane are employed. A molar equivalent amount in excess of about 5 can be employed to help drive the reaction to more complete formation of the halogenated phosphorate.

The oxirane addition reaction is preferably carried out in the presence of the Lewis acid catalysts. For the most part, preferred amounts of the catalysts employed are from about 0.1 percent by weight of the phosphorus intermediate to about 5 percent by weight, most preferably about 0.5 percent by weight.

Pressures, in general, are from ambient atmospheric to elevated such as can be employed with gaseous reactants such as ethylene oxide or chlorine. The elevated pressures include pressures of about 50 psig (i.e., a gauge pressure of about 345 kPa). Preferably, pressures are ambient.

Purification can be by known methods such as by evaporation, distillation and chromatography. Distillation is preferred.

The halogenated phosphorate-containing product can be produced in good yields. Preferably, yields are about 70 percent of theory or greater based on the halogenated phosphorates and most preferably about 80 percent of theory or greater.

The halogenated phosphorate products, especially the mixtures, can have excellent viscosity. Preferably, the viscosity is measured with a Brookfield viscometer at 25° C. with a number 6 spindle submersed with sample in a vial having a width at least 125 percent of the spindle diameter. The spindle is rotated at 100 rotations per minute (i.e., 100 rpm). Preferably, the Brookfield viscosity is about 1000 centipoise (i.e., cP) or lower, more preferably 500 cP or lower.

The halogenated phosphorate product can have excellent thermal stability, which can indicate that when incorporated into a polyurethane foam, especially a flexible foam, the flame-retardant polyurethane foam has little or no scorch. A preferred measure of the thermal stability is by thermogravimetric analysis (i.e., TGA), where the sample tested is continuoualy monitored for weight loss as its temperature is progressively increased in an oven with a nitrogen atmosphere. Preferably, the progressive temperature increase is at a rate of 20° C. per minute from an initial temperature of 20° C. with the sample size initially between 0.010 g and 0.020 g. Under these preferred test conditions, thermogravimetric analyses preferably have a 50 percent weight loss of sample (i.e., $TGA_{50}$) at a temperature of about 200° C. or above, more preferably about 250° C. or above and most preferably about 280° C. or above.

The thermogravimetric analysis at 10 percent weight loss (i.e., $TGA_{10}$) may be used also. The $TGA_{10}$ is otherwise measured as is the $TGA_{50}$. Preferred $TGA_{10}$ values include values found at about 160° C. or above, more preferably about 200° C. or above and most preferably about 230° C. or above.

Odor is a polyurethane production characteristic which may be improved by being reduced or even eliminated. The formation of a by-product such as tetrabromoneopentane at levels of about 1 percent to about 4 percent by weight, may cause the musty odor. Keeping the presence of such a by-product to levels below 1 percent by weight, more preferably 0.5 percent by weight, typically eliminates such an odor in the resulting flame-retardant polyurethane, especially in flexible slabstock foam. The instant process typically avoids formation of such a by-product and thus can contribute to an essentially non-odoriferous foam.

The halogenated phosphorate-containing product is preferably employed as a flame retardant in flexible polyurethane foams in amounts sufficient to produce the desired results, for example, from about 2 to about 20 percent by weight of polyahl of the polyurethane reaction component. In general, components and conditions are such as those known in the art or such as disclosed in copending U.S. patent application Ser. No. 811,086, filed Dec. 19, 1985 (incorporated herein by reference).

SPECIFIC EMBODIMENTS

The following examples further illustrate the invention. Unless otherwise stated, percentages are by weight.

EXAMPLE 1

Preparation of mixture of 60 percent phosphoric acid: (2,2-bis(bromomethyl)propyl)(2-bromoethyl)(2-chloroethyl)ester and 40 percent phosphoric acid: (2-bromoethyl)bis(2-chloroethyl) ester Into a flask are placed 69 g of $PCl_3$ (0.5 mole). It is stirred while 30 g of 2-methyl-2-(hydroxymethyl)-1,3-propanediol (0.25 mole) is added in portions. Upon completion of this addition, 250 ml of methylene chloride is added, and the reaction is purged with nitrogen at 35° C. until HCl ceases to evolve. The mixture is cooled to 10° C. or less in an ice water bath. Next, 76 g of bromine (0.48 mole) in 50 ml of methylene chloride is added dropwise. A light red color is present upon completion of this addition. The mixture is heated to reflux with nitrogen purge, and next it is cooled in a cold water bath. Next, 60 g of ethylene oxide (1.35 mole) in 100 ml of methylene chloride is added dropwise at 40° C. Upon completion of the reaction, some low boilers are distilled off, and the mixture is allowed to cool. Next, 100 ml of dilute base water solution (1 N NaOH) is added, and the mixture is stirred for 10 minutes. The mixture is filtered; the product layer is separated and filtered through some sodium sulfate, and low boilers are removed. A clear oil (156 g) is produced at 76 percent theoretical yield with Brookfield viscosity (Number 6 spindle; 100 rpm) of 250 cP at 25° C. $TGA_{10}$: 249° C.; $TGA_{50}$: 303° C. Elemental analysis: 38.8 percent Br; 12.8 percent Cl; 7.5 percent P.

EXAMPLE 2

Preparation of mixture of 61 percent phosphoric acid: (2,6-dibromohexyl)(2-bromoethyl)(2-chloroethyl) ester and 39 percent phosphoric acid: (2-bromoethyl)(bis(2-chloroethyl)) ester The procedure of Example 1 is followed with the following reagents: 69 g of $PCl_3$ (0.5 mole), 200 ml of methylene chloride, 33.5 g of 1,2,6-trihydroxyhexane (0.25 mole), 80 g of bromine (0.5 mole), 1 ml of $TiCl_4$ and 70 g of ethylene oxide (1.6 mole) in 50 ml of methylene chloride. An oil (171 g) is produced at 82 percent theoretical yield with Brookfield viscosity (Number 6 spindle; 100 rpm) of 200 cP at 25° C. Elemental anlaysis: 47.1 percent Br; 7.0 percent percent Cl; 9.4 percent P.

EXAMPLE 3

Preparation of mixture of 59 percent phosphoric acid: (2,2-bis(bromomethyl)butyl)(2-bromopropyl)(2-chloropropyl) ester and 41 percent phosphoric acid: (3-bromopropyl)bis(2-chloropropyl) ester The procedure of Example 1 is followed with the following reagents: 69 g of $PCl_3$ (0.5 mole), 200 ml of 1,2-dichloroethane, 33.5 g of 2-ethyl-2-(hydroxymethyl)-1,3-propanediol (0.25 mole), 76 g of bromine (0.48 mole), 1 ml of $TiCl_4$ and 80 g of propylene oxide (1.4 mole) in 50 ml of 1,2-dichloroethane. An oil (68 g) is produced at 74 percent theoretical yield with Brookfield viscosity (Number 6 spindle; 100 rpm) of 350 cP at 25° C. $TGA_{10}$: 231° C.; $TGA_{50}$: 281° C. Elemental analysis: 26.4 percent Br; 11.7 percent Cl; 6.8 percent P.

I claim:

1. A process to prepare a halogenated phosphorate-containing product comprising serially contacting
    (A) a triol with a phosphorus trihalide;
    (B) a halogenating agent; and
    (C) an oxirane, under conditions sufficient to prepare the halogenated phosphorate-containing product.
2. The process of claim 1 wherein the triol is a β-neocarbyltriol.
3. The process of claim 2 wherein the phosphorus trihalide is phosphorus trichloride.
4. The process of claim 3 wherein the halogenating agent is elemental bromine.
5. The process of claim 4 wherein the oxirane is selected from the group consisting of ethylene oxide and propylene oxide.
6. The process of claim 5 wherein the yield is about 70 percent of theory or above.
7. The process of claim 6 wherein the yield is about 80 percent of theory or above.
8. The process of claim 1 wherein the halogenated phosphorate-containing product has a Brookfield viscosity of about 1000 cP or lower at 25° C.

* * * * *

UNITED STATES PATENT AND TRADEMARK OFFICE
CERTIFICATE OF CORRECTION

PATENT NO. : 4,774,348

DATED : September 27, 1988

INVENTOR(S) : Chester E. Pawloski

It is certified that error appears in the above-identified patent and that said Letters Patent is hereby corrected as shown below:

Column 1, line 56 please delete "which" and insert -- what --.

Column 1, line 58 please delete "shoudl" and insert -- should --.

Column 2, Figure (C), line 28 please delete "(II) + (III) + 5 R Y$_2$R'O-P$\begin{smallmatrix}O\\\|\end{smallmatrix}\begin{smallmatrix}ORY\\ORZ\end{smallmatrix}$" and insert -- (II) + (III) + 5 (R)Y$_2$R'O-P$\begin{smallmatrix}O\\\|\end{smallmatrix}\begin{smallmatrix}ORY\\ORZ\end{smallmatrix}$ --.

Column 3, line 68 please delete "contains" and insert -- contains a --.

Column 4, line 13 please delete "tribromide. phosphorus" and insert -- tribromide. Phosphorus --.

Column 4, line 23 please delete "subsquent" and insert -- subsequent --.

Column 4, line 55 please delete "epoxie" and insert -- epoxide --.

Column 5, line 15 please delete ", tetrachloride and aluminum tirchloride" and insert -- tetrachloride and aluminum trichloride --.

Column 5, line 60 please delete "continoualy" and insert -- continuously --.

Column 7, line 8 please delete "$_1$(0.5 mole)" and insert -- (0.5 mole) --.

UNITED STATES PATENT AND TRADEMARK OFFICE
CERTIFICATE OF CORRECTION

PATENT NO. : 4,774,348

DATED : September 27, 1988

INVENTOR(S) : Chester E. Pawloski

It is certified that error appears in the above-identified patent and that said Letters Patent is hereby corrected as shown below:

Column 7, line 14 please delete "anlaysis" and insert -- analysis --.

Column 7, line 15 please delete "percent percent" and insert -- percent --.

Signed and Sealed this

Nineteenth Day of December, 1989

Attest:

JEFFREY M. SAMUELS

Attesting Officer     Acting Commissioner of Patents and Trademarks